US011854670B2

(12) United States Patent
Georgopoulos et al.

(10) Patent No.: US 11,854,670 B2
(45) Date of Patent: Dec. 26, 2023

(54) RUNNING MULTIPLE EXPERIMENTS SIMULTANEOUSLY ON AN ARRAY OF CHEMICAL REACTORS (71) Applicant: INTERNATIONAL BUSINESS MACHINES CORPORATION, Armonk, NY (US)

(72) Inventors: Leonidas Georgopoulos, Zurich (CH); Aleksandros Sobczyk, Ruschlikon (CH); Alain Claude Vaucher, Zurich (CH); Philippe Schwaller, Duedingen (CH); Vishnu Harikrishnan Nair, Edappally (IN); Joppe Geluykens, Zurich (CH); Teodoro Laino, Ruschlikon (CH)

(73) Assignee: International Business Machines Corporation, Armonk, NY (US)

( * ) Notice: Subject to any disclaimer, the term of this patent is extended or adjusted under 35 U.S.C. 154(b) by 698 days.

(21) Appl. No.: 16/995,858

(22) Filed: Aug. 18, 2020

(65) Prior Publication Data

US 2022/0059192 A1     Feb. 24, 2022

(51) Int. Cl.
*G16C 20/10* (2019.01)
*B01J 19/00* (2006.01)
*G16C 20/90* (2019.01)

(52) U.S. Cl.
CPC .......... *G16C 20/10* (2019.02); *B01J 19/0033* (2013.01); *B01J 19/0046* (2013.01); *G16C 20/90* (2019.02);
(Continued)

(58) Field of Classification Search
CPC ................ B01J 19/0046; B01J 19/0033; B01J 2219/00695; B01J 2219/00997;
(Continued)

(56) References Cited

U.S. PATENT DOCUMENTS

| 8,934,994 B1 | 1/2015 | Lee |
| 10,332,619 B2 | 6/2019 | Giri |

(Continued)

FOREIGN PATENT DOCUMENTS

| WO | 2019086325 A1 | 5/2019 |
| WO | 2019137954 A1 | 7/2019 |

(Continued)

OTHER PUBLICATIONS

IBM, List of IBM Patents or Patent Applications Treated as Related, Appendix P, dated Sep. 4, 2020, 2 pages.

(Continued)

*Primary Examiner* — Shogo Sasaki
(74) *Attorney, Agent, or Firm* — L. Jeffrey Kelly (57) ABSTRACT

A method for executing multiple chemical experiments in parallel may be provided. The method comprises receiving a list of actions to be performed for synthesizing a chemical product. Thereby, the actions correspond to at least two chemical partial reactions and the list comprises a delimiter symbol separating two chemical partial reactions, determining identical chemical partial reactions, and building a reaction commonality tree (RCT) of the chemical reactions. Furthermore, the method comprises executing a plurality of the identical chemical partial reactions independent of a sequence of chemical partial reactions of the reaction commonality tree only once. Each of the identical chemical partial reactions is executed in a different chemical reactor and each resulting intermediate product has a quantity of the sum of the related identical chemical partial reactions. The method also comprises, storing the intermediate chemical products in a separate container, and executing remaining chemical partial reactions according to the RCT.

20 Claims, 7 Drawing Sheets (52) U.S. Cl.
CPC ............. *B01J 2219/00038* (2013.01); *B01J 2219/00195* (2013.01); *B01J 2219/00695* (2013.01)

(58) Field of Classification Search
CPC .... B01J 2219/00995; B01J 2219/00033; B01J 2219/00029; B01J 19/0093; B01J 2219/00031; B01J 2219/00038; B01J 2219/00195; G16C 20/10; G16C 20/09
See application file for complete search history.

(56) References Cited

U.S. PATENT DOCUMENTS

| | | | |
|---|---|---|---|
| 10,589,248 B1 | 3/2020 | Doris | |
| 11,132,621 B2* | 9/2021 | Botea | G16C 20/90 |
| 2002/0049548 A1* | 4/2002 | Bunin | G16C 20/90 |
| | | | 702/30 |
| 2002/0111782 A1* | 8/2002 | Klaffke | G05B 17/02 |
| | | | 703/12 |
| 2004/0003000 A1 | 1/2004 | Smith | |
| 2005/0246316 A1* | 11/2005 | Lawson | G16C 20/70 |
| 2009/0024575 A1* | 1/2009 | Wagner | G16C 20/10 |
| 2009/0228445 A1 | 9/2009 | Gangal | |
| 2011/0213499 A1 | 9/2011 | Sturmer | |
| 2013/0041683 A1* | 2/2013 | Boissel | G16B 40/20 |
| | | | 705/2 |
| 2016/0103979 A1 | 4/2016 | Giri | |
| 2018/0046930 A1 | 2/2018 | Kossarian | |
| 2018/0093245 A1 | 4/2018 | Colgan | |
| 2019/0147370 A1* | 5/2019 | Botea | G16C 20/90 |
| | | | 706/11 |
| 2019/0233751 A1 | 8/2019 | Medoff | |
| 2020/0050947 A1* | 2/2020 | Kishimoto | G06N 5/025 |
| 2020/0066552 A1 | 2/2020 | Susa | |
| 2020/0168302 A1* | 5/2020 | Isayev | G06N 3/045 |
| 2022/0058337 A1 | 2/2022 | Georgopoulos | |
| 2022/0059193 A1 | 2/2022 | Georgopoulos | |

FOREIGN PATENT DOCUMENTS

| | | |
|---|---|---|
| WO | 2019179887 A1 | 9/2019 |
| WO | 2022037985 A1 | 2/2022 |

OTHER PUBLICATIONS

Coley et al., "A robotic platform for flow synthesis of organic compounds informed by AI planning", Research Article Summary, Science 365, Aug. 9, 2019, pp. 1-11.

Mysore et al., "Automatically Extracting Action Graphs from Materials Science Synthesis Procedures", Nov. 28, 2017, Workshop on Machine Learning for Molecules and Materials at NIPS 2017, Long Beach, CA, USA, 11 pages.

Nicolaou et al., "Context Aware Data-Driven-Retrosynthetic Analysis", Journal of Chemical Information and Modeling, Published Apr. 13, 2020, pp. 2728-2738.

Vaucher et al., "Automated extraction of chemical synthesis actions from experimental procedures", nature communications, Article, 2020, pp. 1-11.

Vaucher et al., "Inferring experimental procedures from text-based representations of chemical reactions", nature communications, Article, 2021, pp. 1-11.

Mell et al., "The NIST Definition of Cloud Computing", Recommendations of the National Institute of Standards and Technology, Special Publication 800-145, Sep. 2011, 7 pages.

* cited by examiner

RUNNING MULTIPLE EXPERIMENTS SIMULTANEOUSLY ON AN ARRAY OF CHEMICAL REACTORS

BACKGROUND

The invention relates generally to a method for executing multiple chemical experiments, and more specifically, to a method for executing multiple chemical experiments in parallel on an array of chemical reactors. The invention relates further to a chemical reaction control system for executing multiple chemical experiments in parallel on an array of chemical reactors, and program products.

SUMMARY

According to one aspect of the present invention, a method for executing multiple chemical experiments in parallel on an array of chemical reactors may be provided. The method may include receiving a list of actions to be performed for synthesizing a chemical product, where the list of actions may correspond to at least two chemical partial reactions, where the list may include a delimiter symbol separating each two chemical partial reactions in the list of actions, determining identical chemical partial reactions in the list of actions, and building a reaction commonality tree of the chemical partial reactions according to subsequent points in time in the list of actions.

Additionally, the method may include controlling and executing a plurality of the identical chemical partial reactions independent of a sequence of chemical partial reactions of the reaction commonality tree only once, where each of the plurality of identical chemical partial reactions may be executed in a different reactor of the array of chemical reactors, where each resulting intermediate product may have a quantity required by at least the sum of the related identical chemical partial reactions, storing each complete quantity of identical related intermediate chemical products in a separate container, and controlling an executing the chemical partial reactions according to the reaction commonality tree, thereby using at least in parts the stored intermediate chemical products.

According to another aspect of the present invention, a chemical reaction control system for executing multiple chemical experiments in parallel on an array of chemical reactors may be provided. The chemical reaction control system may include receiving means adapted for receiving a list of actions to be performed for synthesizing a chemical product, where the list of actions corresponds to at least two chemical partial reactions, where the list of actions may include a delimiter symbol separating each two chemical partial reactions in the list of actions, determining means adapted for determining identical chemical partial reactions in the list of actions, and building means adapted for building a reaction commonality tree of the chemical partial reactions according to subsequent points in time in the list of actions.

Moreover, the chemical reaction control system may include a first controller means adapted for controlling an execution of a plurality of the identical chemical partial reactions independent of a sequence of chemical partial reactions of the reaction commonality tree only once, where each of the plurality of identical chemical partial reactions may be executed in a different reactor of the array of chemical reactors, where each resulting intermediate product may have a quantity required by at least the sum of the related identical chemical partial reactions, and storage means adapted for storing each complete quantity of identical related intermediate chemical products in a separate container, and a second controller means adapted for controlling an execution of the chemical partial reactions according to the reaction commonality tree, thereby using at least in parts the stored intermediate chemical products.

The proposed method for executing multiple chemical experiments in parallel on an array of chemical reactors may offer multiple advantages, technical effects, contributions and/or improvements:

The proposed concept allows an acceleration and automation of at least in parts complex chemical reactions using in an array of chemical reactors (which may be a part of one or more chemical robots). Often, longer, more complex chemical reactions require intermediate steps, denoted here as partial chemical reactions, producing intermediate products which may be used in later stages of the longer, more complex chemical reactions. Thereby, in different stages of a longer list of partial chemical reactions, a repetition of the production of the intermediate product may be required. The here proposed concept addresses this situation advantageously by pulling identical partial chemical reactions together, although, in the sequence of the list of actions they are, so to speak, out of order, and execute the partial chemical reaction only once, thereby producing the complete required amount of the intermediate product for the complete list or lists of actions.

Different chemical reactions may be executed in parallel on different ones of the reactors of the array of chemical reactors, thereby increasing the total throughput of experiments through the reaction chambers significantly. This way, many more chemical experiments may be run in parallel, thereby increasing the productivity of the staff and the usage level of the equipment advantageously. Also the use of resources may be improved because executing a chemical reaction only once instead of several times may help to reduce the consumption of chemicals, energy and washing ingredients.

This may result in a faster development of new pharmaceutical products and may help to accelerate the depreciation time of the often very expensive equipment.

In the following, additional embodiments of the inventive concept will be described.

According to one embodiment, the method may include assigning a required number of the chemical reactors to one of the partial chemical reactions. Preforming one chemical reaction may include several sub-reaction-steps where a stable intermediate product is available. Hence, the reaction needs to be performed and has a flow of different sub-steps. If, e.g., a first reactant may need to be mixed with a catalyst under certain predefined environmental conditions before it may react with a second reactant under different predefined environmental conditions, the first sub-step may be performed in one reactor and the second sub-step may be performed in a second reactor.

According to one permissive embodiment of the method, the assigning may be performed under the constraint indicative of having more chemical partial reactions than chemical reactors may be available. In such a case, these intermediate products, which may be more dangerous, may be produced at a later time, whereas such intermediate products being more stable can be produced earlier in a longer, multi-step chemical process.

According to one embodiment of the method, the steps of receiving, determining, building and assigning may be performed by a program service. This may be a remote service. Separating the technical domains of controlling an at least in parts mechanical system, i.e., the chemical robot with its array of substances, and the controlling information technology may have the advantage that each domain specialist may focus on his/her core competency. Additionally, those controlling the operation of the chemical robot may be located remote to the actual, potentially dangerous, chemical experiment.

The remote program service may be provided by a proprietary environment, but may also advantageously be provided by a cloud computing system making use of all advantages of a cloud-computing deployment.

According to one possible embodiment of the method, the delimiter represents a store, e.g., in the form of the term "STORE". Wherever this keyword is found in the string of the chemical program, an intermediate product may be available which can be kept in a special intermediate product container for later use in the chemical reaction process steps. Thus, an intermediate product may be produced in excess of the amount actually required if the same intermediate product may be required time-wise later if also other chemical reactions/programs have been received or are selected. This way, the overall process comprising a plurality of chemical programs may be optimized.

According to preferred embodiments of the method, the chemical reactors may be selected out of the group comprising batch reactors, continuous stirred tank reactors, plug flow reactors, semi-batch reactors, and microfluidic reactors. Reactors of these types are known in the field of automated or semi-automatic chemical experiments. Additionally, also different types of reactor types may be used in a mixed mode as long as they may be connectable to the area of containers comprising the chemical reactants.

According to one preferred embodiment, the method may also include determining the quantity required by at least the sum of the related identical chemical partial reactions according to a function comprising at least one out of the following arguments: the sum of quantities required to synthesize the respective intermediate product. It is also possible to use a first multiplication factor if the intermediate product is a solid compound, a second multiplication factor if the intermediate product is a liquid, and/or a third multiplication factor received via a user interface. This way, at least the sum of quantities required to synthesize the intermediate products for the chemical programs in question may be produced, thereby reflecting a loss of reactants due to being left in one of the reactors and be washed out during an intermediate cleaning process.

According to one optional embodiment, the method may also include producing one of the intermediate products in parallel in different ones of the chemical reactors. This may be done due to a limited capacity of one of the reactors or to speed up the production of the selected one of the intermediate products in order to reach a required amount of the specific intermediate product.

According to an advanced embodiment of the method, the chemical product, in particular the end product, may be a plurality of chemical products. This may, in particular, be interesting in the field of oil refineries or similar experimental environments.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain means for storing, communicating, propagating or transporting the program for use, by, or in connection, with the instruction execution system, apparatus, or device.

BRIEF DESCRIPTION OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Preferred embodiments of the invention will be described, by way of example only, and with reference to the following drawings.

DETAILED DESCRIPTION

Performing chemical experiments for a synthesis of new molecules in the chemical, biochemical or pharmaceutical area is time-consuming and typically labor-intensive. In order to partially automate such synthesis experiments, chemical robots have been introduced allowing a software controlled experiment designed in which a limited number of ingredients for the experiments may react, e.g., a reaction chamber to produce a designed experiment output instead of conducting such wet-lab experiments by humans. Such chemical robots typically source the reactants from an array of potential reactants in which the reactants are stored. Time is a major constraint in conducting the multitude of chemical experiments. However, due to the many required manual tasks to control such semi-automated experiment environments, it cannot be guaranteed that the equipment makes best use of the time available.

In this context, some documents have been published for processing biomass. Thereby, a process for the production cellulosic ethanol with 100% biogenic carbon content is described. Several tools for a partial process automation are involved.

Additionally, a method for analyzing process streams comprising five or more different hydrocarbon-containing components where at least one process is streamlined and is operatively connected to an online IR spectrometer and to an online gas chromatograph.

However, a disadvantage of known solutions is that they do not disclose how a chemical robot comprising a plurality of chemical reactors can be used to perform a plurality of reaction executions if multiple of such reaction executions may have identical initial reaction steps. Hence, a sub-optimal use of synthesis robots may be the result. Hence, in order to save time and resources, there is a need to automatically detect common reaction subtrees and execute corresponding reactions with only little overhead.

In the context of this description, the following conventions, terms and/or expressions may be used:

The term 'array of chemical reactors' may denote a plurality of different or identical chemical reactors connectable to an array of containers comprising reactants for a plurality of chemical experiments. In general, a chemical reactor may be an enclosed volume in which a chemical reaction may take place. A chemical reactor may also be part of a chemical robot. Actually, a chemical robot may include a plurality of chemical reactors and containers comprising reactants, as well as, containers to store intermediate products, as well as, the end product.

The term 'list of actions' may denote process steps required to produce a chemical end product. In order to achieve this objective, a plurality of intermediate products may be produced in the sequence of actions to arrive at the chemical end product.

The term 'chemical product' may denote a result of a chemical reaction or a series of chemical reactions. In order to receive the chemical end product it may be required to produce one or more intermediate products along the overall reaction process.

The term 'chemical partial reaction' may denote a sub-step of a complete chemical reaction to produce a chemical end product. Each chemical partial reaction may provide a stable (or at least semi-stable) intermediate product which may be used for further chemical partial reactions on the way to the chemical end product.

The term 'delimiter symbol' may denote a specific symbol of combinations of symbols, e.g., a string of predefined characters (staring with one character as a minimum), in order to separate different chemical partial reactions. Whenever a delimiter symbol is found after a chemical partial reaction the resulting intermediate product may be stable and storable.

The term 'identical chemical partial reaction' may denote a chemical partial reaction requiring identical reactants and resulting in the same intermediate product. Hence, identical chemical partial reactions may be required along the complete experiment process but at different points in time.

The term 'reaction commonality tree' may denote a data structure indicative of the sequence of partial chemical reactions and their related sequence of times at which they need to be performed in the overall chemical experiment.

The term 'cloud computing system' may denote a remote computing system delivering an application service under the paradigm of cloud computing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

In the following, a detailed description of the figures will be given. All instructions in the figures are schematic. Firstly, a block diagram of an embodiment of the inventive method for executing multiple chemical experiments in parallel on an array of chemical reactors is given. Afterwards, further embodiments, as well as embodiments of the chemical reaction control system for executing multiple chemical experiments in parallel on an array of chemical reactors, will be described.

Figure 1:
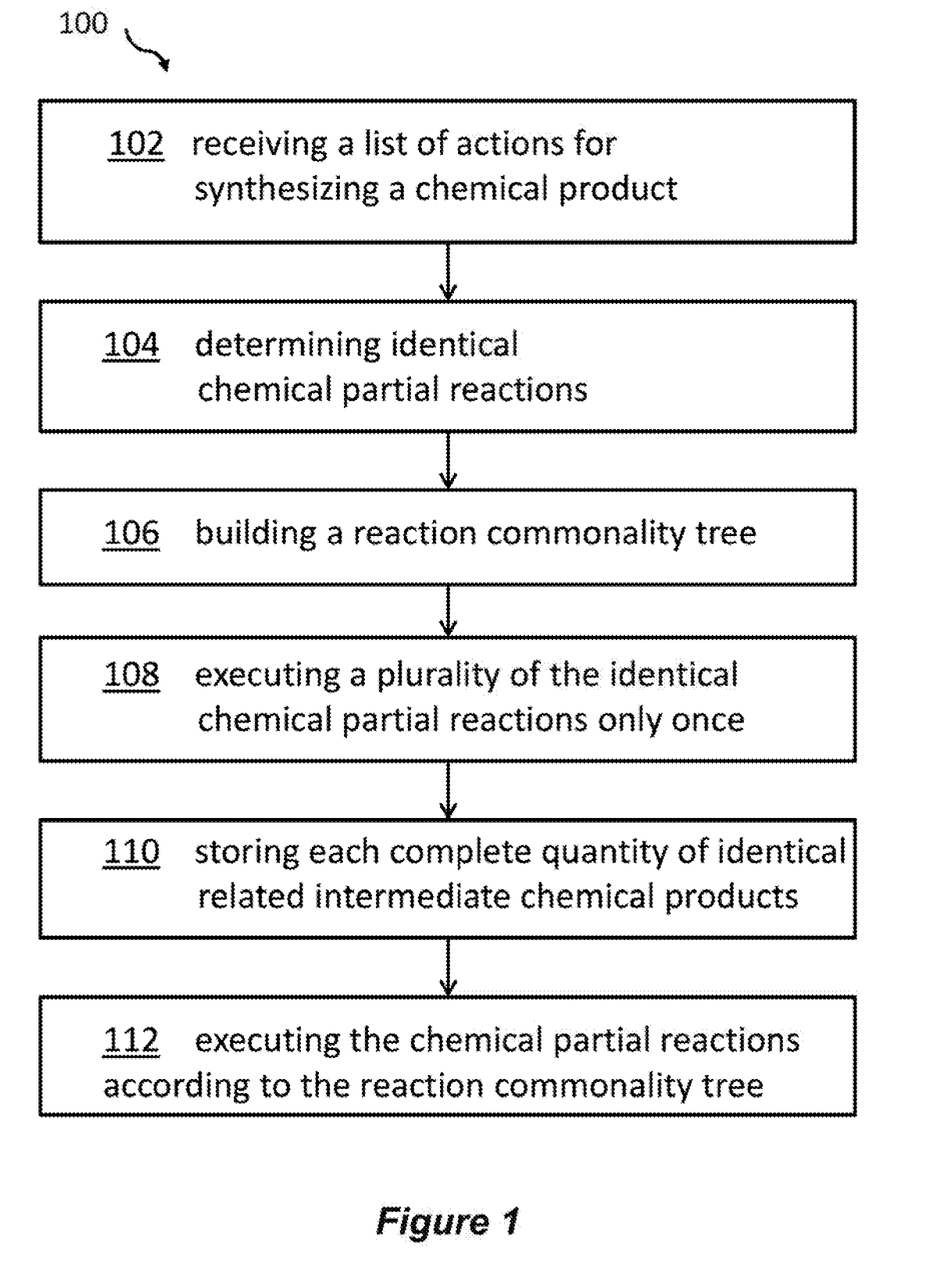
FIG. 1 shows a block diagram of an embodiment of the inventive method for executing multiple chemical experiments in parallel on an array of chemical reactors, according to an embodiment.

FIG. 1 shows a block diagram of a preferred embodiment of the method 100 for executing multiple chemical experiments in parallel on an array of chemical reactors, according to an embodiment. The method 100 includes receiving, 102, a list of actions to be performed, in particular, using the chemical reactors, for synthesizing a chemical end product (or a plurality of end products). Thereby, the list of actions may correspond to at least two chemical partial reactions. Furthermore, the list may include a delimiter symbol, e.g., STORE command, separating each two chemical partial reactions in the list of actions. It may be noted that also other delimiter symbols or commands may be used.

The method 100 includes further determining, 104, identical chemical partial reactions in the list of actions; building, 106, a reaction commonality tree of the chemical partial reactions according to subsequent points in time in the list of actions; and executing 108, a plurality of the identical chemical partial reactions independent of a sequence of chemical partial reactions of the reaction commonality tree only once. Thereby, each of the plurality of identical chemical partial reactions can be executed in a different one of the array of chemical reactors. Additionally, each resulting intermediate product has a quantity required of at least the sum of the related identical chemical partial reactions requiring the intermediate product.

Furthermore, the method 100 includes storing, 110, each complete quantity of identical related intermediate chemical products in a separate container; and executing, 112, the chemical partial reactions according to the reaction commonality tree, thereby using at least in parts the stored intermediate chemical product(s). From a program service perspective not all steps of the method may be performed, some of the method steps may only be controlled; this applies in particular to those sub-steps of the method being performed by the chemical robot.

Figure 2:
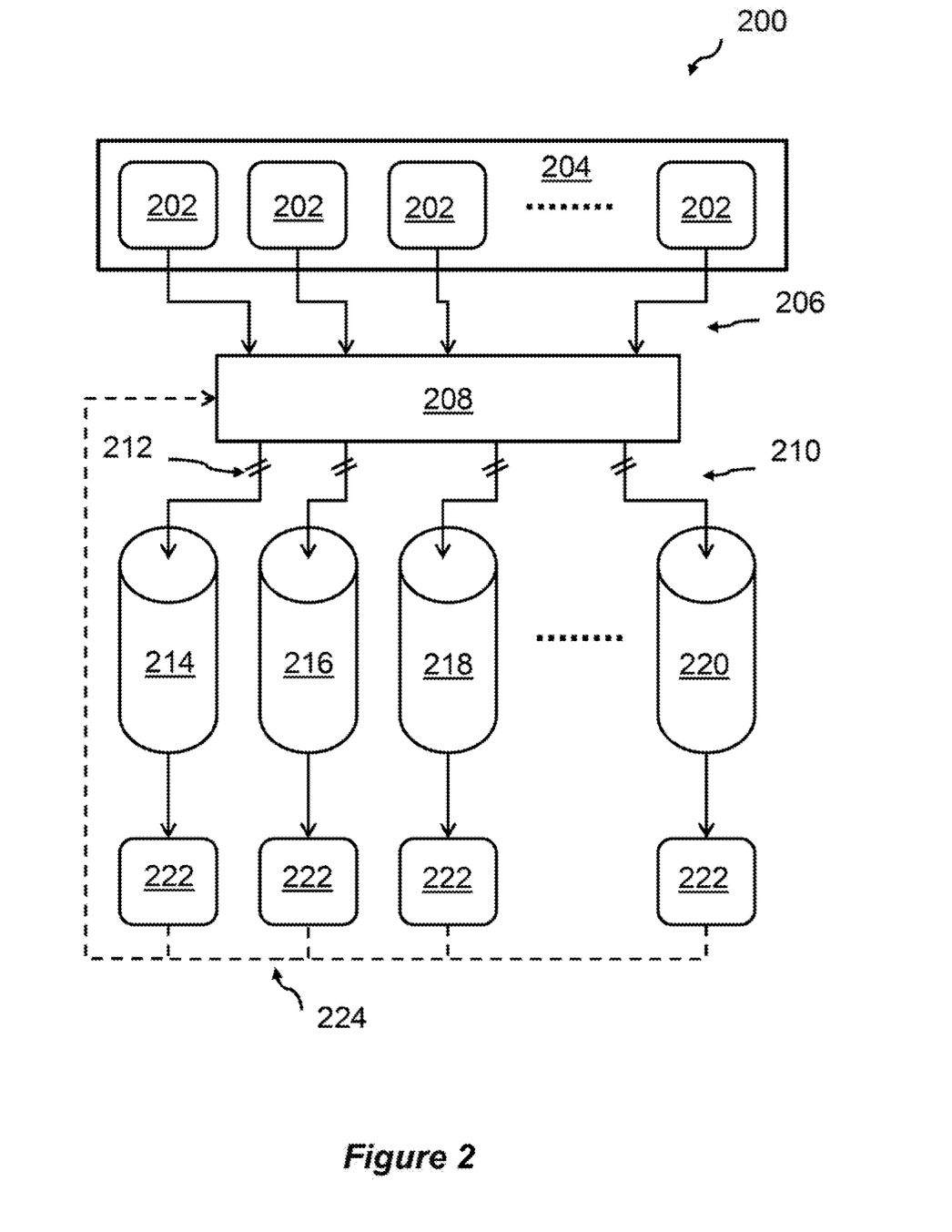
FIG. 2 shows a block diagram of an array of reactant container together with an array of chemical reactors, according to an embodiment.

FIG. 2 shows a block diagram of a chemical reaction system 200 and an array 204 of a plurality of reactant containers 202 together with an array of chemical reactors 214, 216, 218, . . . , 220, according to an embodiment. The reactant containers 202 are individually connected via pipe layer 206 to a valve and direction unit 208 which is on the other side connected via pipe layer 210 to one or more pipes per chemical reactor 214, 216, 218, . . . , 220. The parallel lines 212 indicate that more than one pipe may exist between the valve and direction unit 208 and the individual chemical reactors 214, 216, 218, . . . , 220. On the output side of the chemical reactors 214, 216, 218, . . . , 220—e.g., connected in a 1:1 fashion—a plurality of chemical reaction product containers 222 exist. These product containers 222 may also be used for intermediate products from individual ones of the chemical reactors 214, 216, 218, . . . , 220. Additionally, there may be pipe connections 224 between the product containers 222 and the valve and direction unit 208 in order to use intermediate products from the product containers 222 for subsequent reactions in the chemical reactors 214, 216, 218, . . . , 220 to finally produce the chemical (end) product.

Figure 3:
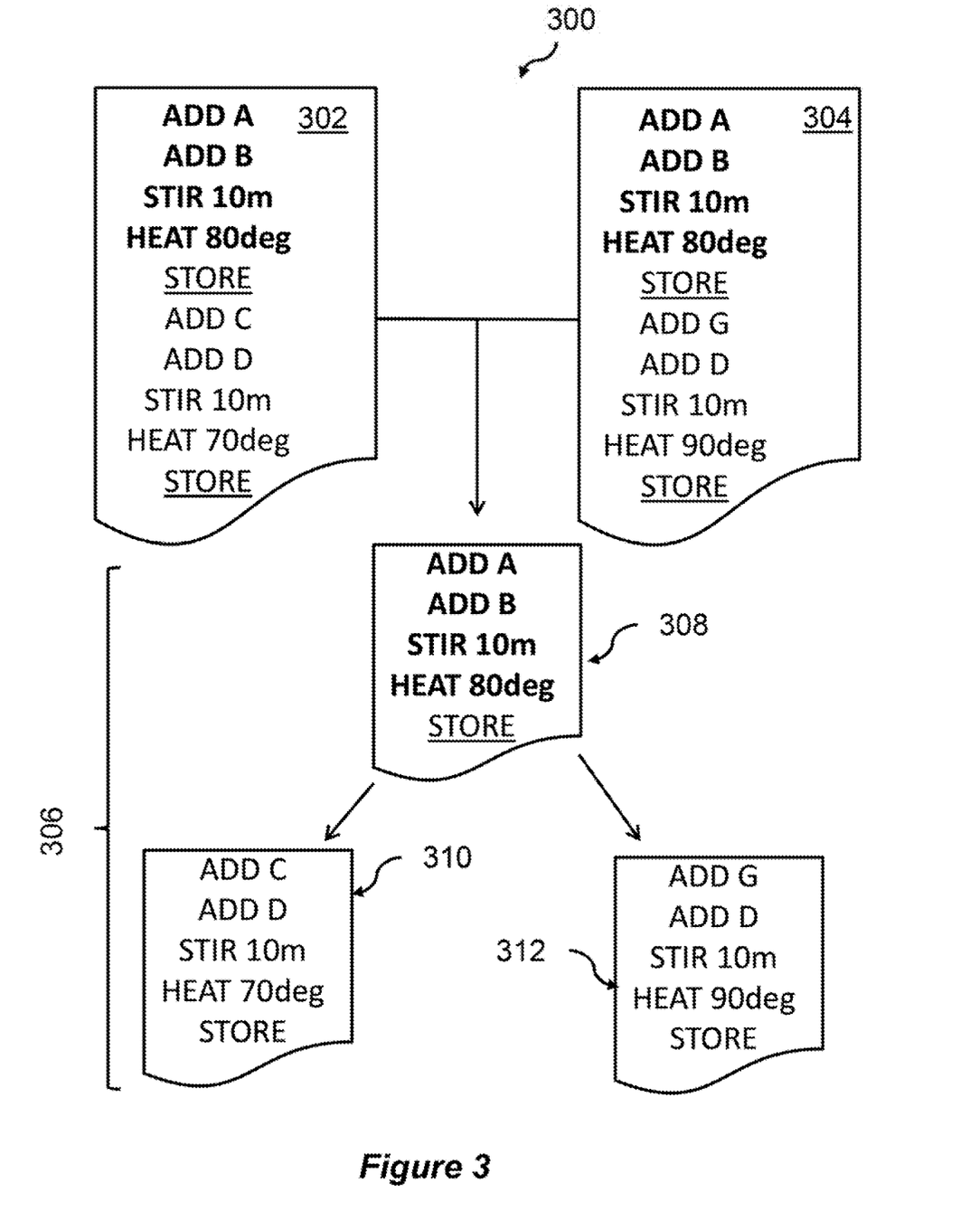
FIG. 3 shows a block diagram of an embodiment of a reaction commonality tree, according to an embodiment.

FIG. 3 shows a block diagram 300 of an embodiment of a reaction commonality tree 306, according to an embodiment. In this case, two lists of actions 302, 304, e.g., chemical programs, are shown in the top portion of FIG. 3. As can be seen, the first 4 actions are identical in the first list of actions 302 and the second list of actions 304 (ADD A, ADD, B, STIR 10 m, HEAT 80 deg). Exemplary, this may be interpreted as "add reactant A, add reactant B, stir the mixture for 10 minutes and heated up to 80° C.". After the "STORE", the list of actions differs between the first list of actions 302 and the second list of actions 304. However, the "STORE" suggests that at this point a stable intermediate product has been produced. A multitude of action commands, such as, ADD, STIR, DRY, MIX, etc., may be used.

In the lower part of FIG. 3, the reaction commonality tree 306 is shown comprising a sub-list 308 of actions describing a partial chemical reaction based on the first four common actions (as described above). The so produced intermediate product may be used for both leaves of the reaction commonality tree 306 as list of actions 310 and list of actions 312. It is understandable that this reaction commonality tree 306 is only a simple example making the fundamental principle comprehensible and that much more complex reaction commonality trees may exist with a much higher number of partial chemical reactions, so that the number of leaves and branches of the reaction commonality tree is much higher.

However, it should be understood that whenever a "STORE" command is shown in any of the list of actions at least one of the chemical reactors 214, 216, 218, . . . , 220 may deliver at least an intermediate product into one or more of the product containers 222. It should also be understood that the amount of the intermediate product at the root of the reaction commonality tree 306 shall be enough to be used for both lower level partial chemical reactions described by the action list 310 and 312. There can also be a situation in which different partial chemical reactions are executed in parallel in different chemical reactors producing different intermediate products to be used as different times according to the reaction commonality tree 306.

Figure 4:
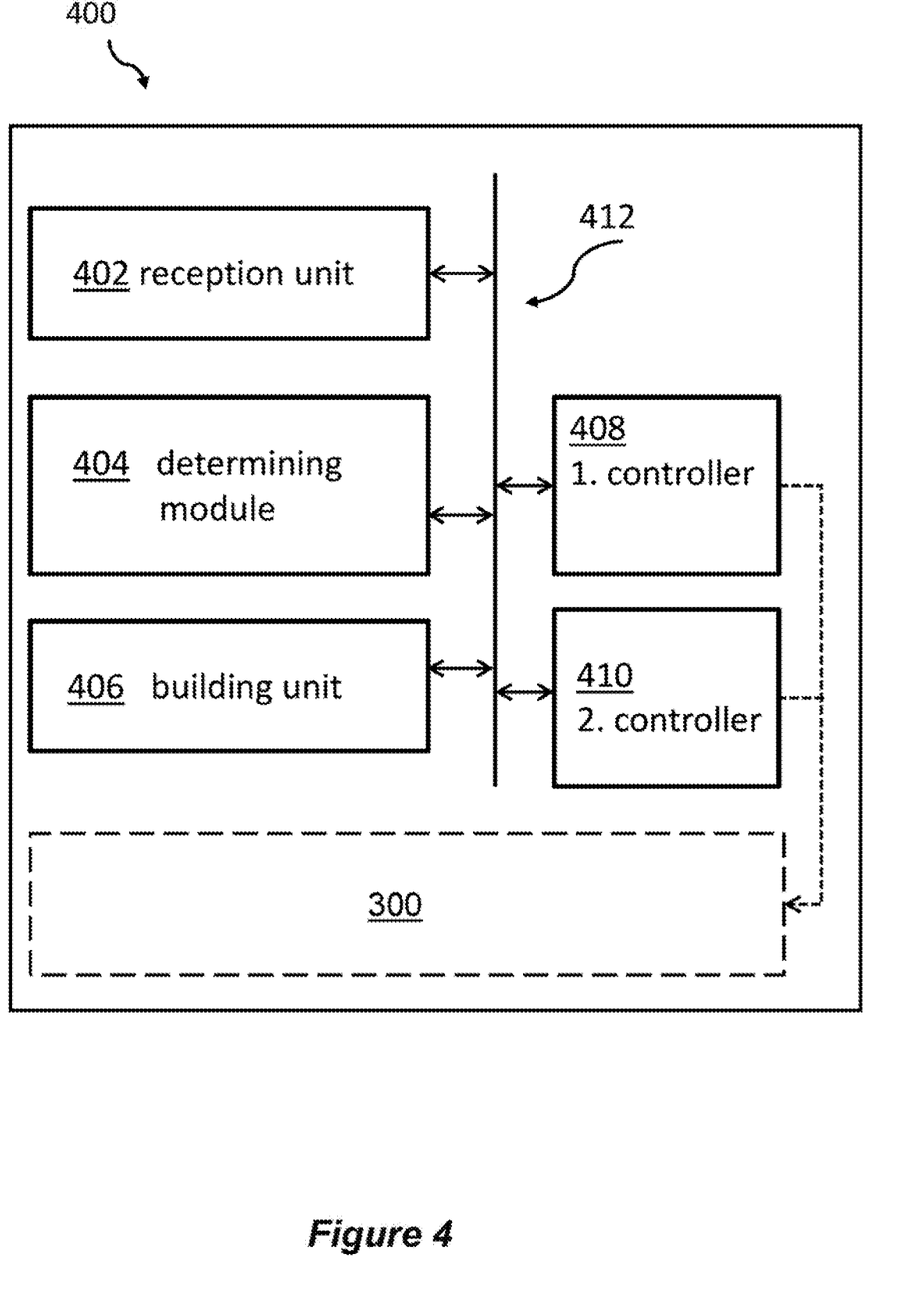
FIG. 4 shows a diagram of an embodiment of a chemical reaction control system for executing multiple chemical experiments in parallel on an array of chemical reactors, according to an embodiment.

For completeness reasons, FIG. 4 shows a diagram of an embodiment of the chemical reaction control system 400 for executing multiple chemical experiments in parallel on an array of chemical reactors. The chemical reaction system 400 includes receiving means, in particular a reception unit 402, adapted for receiving a list of actions to be performed for synthesizing a chemical product. Thereby, the list of actions corresponds to at least two chemical partial reactions and the list can include one or more (typically identical) delimiter symbol/s separating each two chemical partial reactions in the list of actions.

Additionally, the chemical reaction system 400 includes determining means, in particular determination module 404, adapted for determining identical chemical partial reactions in the list of actions, and building means—in particular building unit 406—adapted for building a reaction commonality tree of the chemical partial reactions according to subsequent points in time in the list of actions.

Furthermore, the chemical reaction control system 400 includes first execution means, in particular a first execution controller 408, adapted for controlling an execution of a plurality of the identical chemical partial reactions independent of a sequence of chemical partial reactions of the reaction commonality tree only once. Thereby, each of the plurality of identical chemical partial reactions is executed in a different reactor of the array of chemical reactors, where each resulting intermediate product has a quantity required by at least the sum of the related identical chemical partial reactions. The chemical reaction control system also includes storage means, in particular implemented as a portion of the chemical reaction system 200, adapted for storing each complete quantity of identical related intermediate chemical products in a separate container, and second execution means, in particular a second execution controller 410, adapted for controlling an execution of the chemical partial reactions according to the reaction commonality tree, thereby using at least in parts the stored intermediate chemical products.

It may also be mentioned that the reception unit 402, the determination module 404, the building unit 406, the first execution controller 408 and the second execution controller 410 are communicatively coupled for an exchange of electrical signals and messages to enable the functioning of the complete chemical reaction control system 400 and the connected chemical reaction system 200. In particular, the first and the second execution controller 408, 410 can be connected to a plurality of values and sensors and other components like heaters and stirring units (not shown) of the chemical reaction system 200. Alternative, the modules and unit may can also be connected via a chemical reaction control system internal bus system 412.

Figure 6:
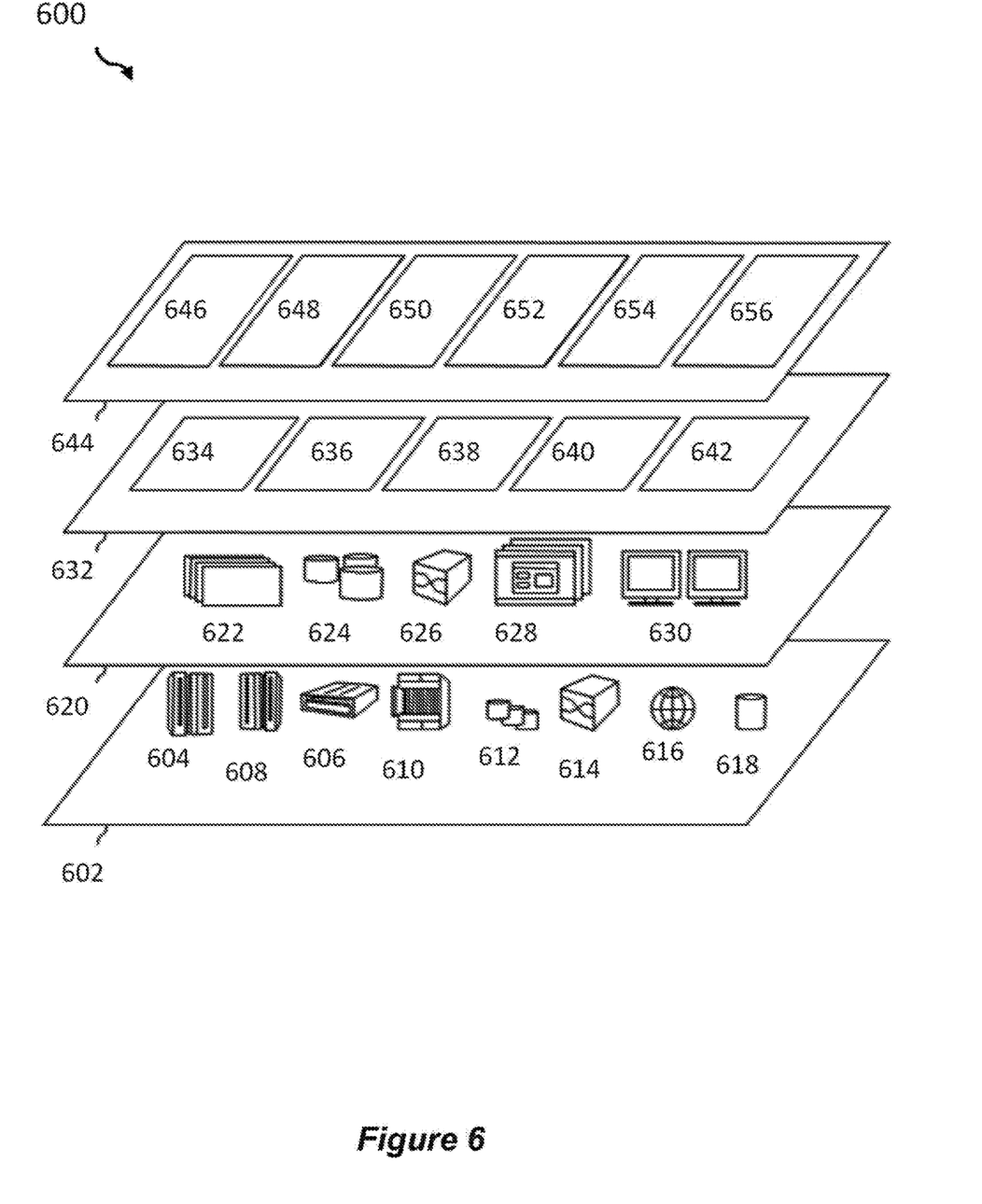
FIG. 6 shows abstraction model layers according to an embodiment of the present invention.
Figure 7:
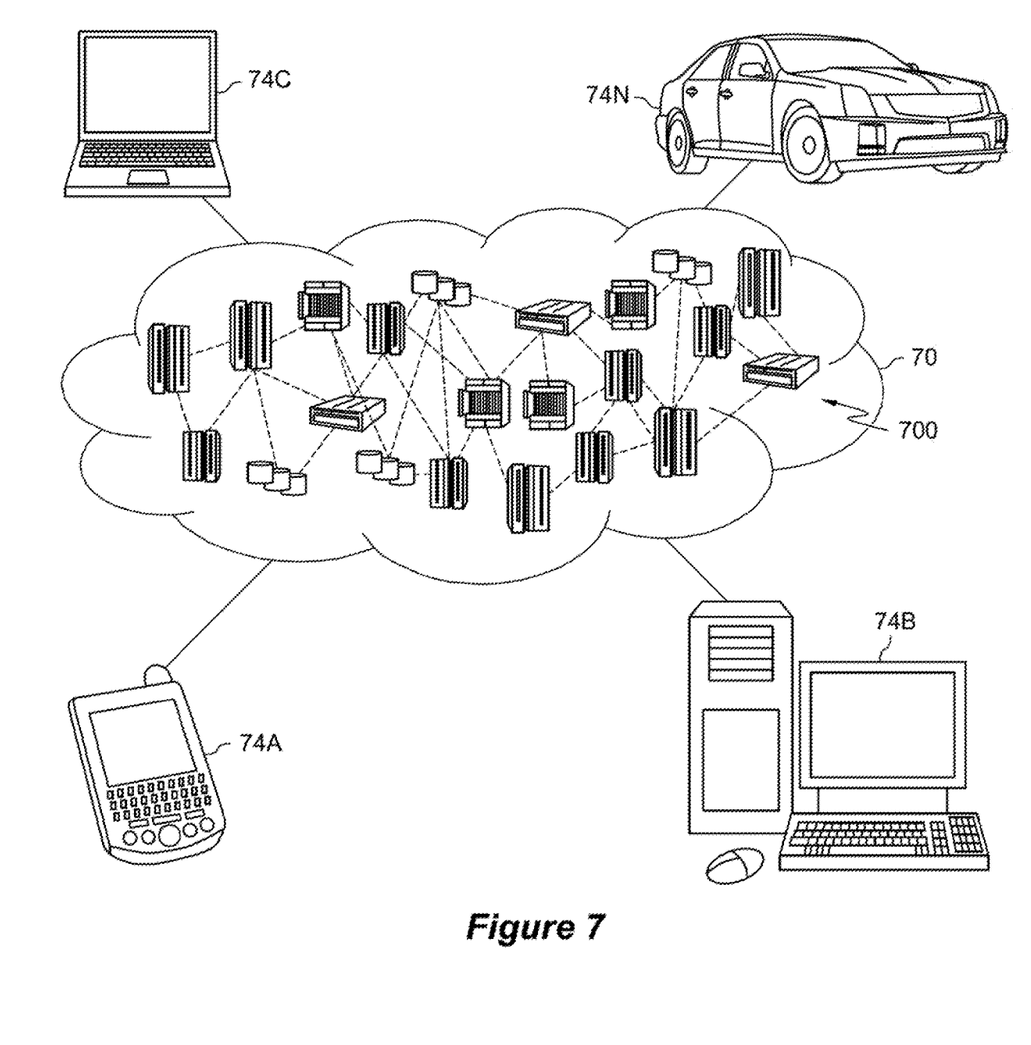
FIG. 7 shows a cloud computing environment in which at least parts of the inventive concept may be deployed, according to an embodiment.

Before turning to FIG. 5, a set of functional abstraction layers 600 provided by cloud computing environment 700 (as shown in FIG. 7) is shown in FIG. 6 and illustrates how parts of the inventive concept—in particular the above-mentioned program service—may be deployed. It should be understood in advance that the components, layers, and functions shown in FIG. 6 are intended to be only illustrative and embodiments of the invention are not limited thereto. As depicted, the following layers and corresponding functions are provided: hardware and software layers 602 include hardware and software components. Examples of hardware components include: mainframes 604; servers 606; RISC (Reduced Instruction Set Computer) architecture-based servers 608; blade servers 610; storage devices 612; networks and networking components 614. In some embodiments, software components include network application server software 616 and/or database software 618.

A virtualization layer 620 provides an abstraction layer from which the following examples of virtual entities may be provided: virtual servers 622; virtual storage 624; virtual networks 626, including virtual private networks; virtual applications and operating systems 628; and virtual clients 630.

In one example, management layer 632 may provide the functions described below. Resource provisioning 634 provides dynamic procurement of computing resources and other resources that are utilized to perform tasks within the cloud computing environment. Metering and pricing 636 provide cost tracking as resources are utilized within the cloud computing environment, and billing or invoicing for consumption of these resources. In one example, these resources may comprise application software licenses. Security provides identity verification for cloud consumers and tasks as well as protection for data and other resources. User portal 638 provides access to the cloud computing environment for consumers and system administrators. Service level management 640 provides cloud computing resource allocation and management such that required service levels are met. Service Level Agreement (SLA) planning and fulfillment 642 provides pre-arrangement for, and procurement of, cloud computing resources for which a future requirement is anticipated in accordance with an SLA.

Workload layer 644 provides examples of functionality for which the cloud computing environment may be utilized. Examples of workloads and functions which may be provided from this layer include: mapping and navigation 646; software development and lifecycle management 648; virtual classroom education delivery 650; data analytics processing 652; transaction processing 654; and the chemical reaction control system 656, for example the chemical reaction control system 400 in FIG. 4.

Figure 5:
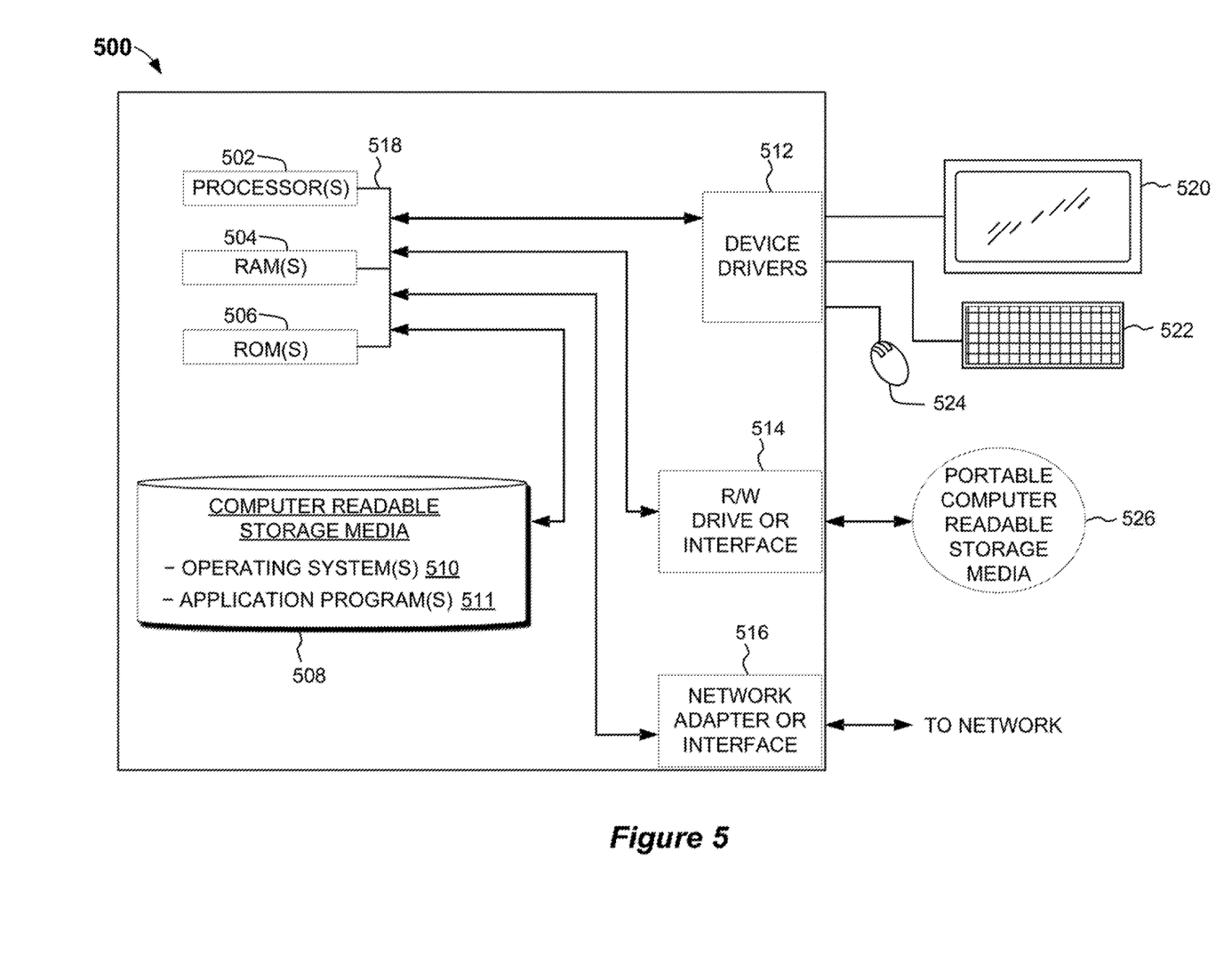
FIG. 5 shows an embodiment of a computing system comprising the chemical reaction control system according to FIG. 4, according to an embodiment.

Embodiments of the invention may be implemented together with virtually any type of computer, regardless of the platform being suitable for storing and/or executing program code. FIG. 5 shows, as an example, a computing device 500 suitable for executing program code related to the proposed method.

The computing device 500 is only one example of a suitable computer system, and is not intended to suggest any limitation as to the scope of use or functionality of embodiments of the invention described herein, regardless, whether the computing device 500 is capable of being implemented and/or performing any of the functionality set forth hereinabove. In the computing device 500, there are components, which are operational with numerous other general purpose or special purpose computing system environments or configurations. Examples of well-known computing systems, environments, and/or configurations that may be suitable for use with computing device 500 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. The computing device 500 may be described in the general context of computer system-executable instructions, such as program modules, being executed by the computing device 500. Generally, program modules may include routines, programs, objects, components, logic, data structures, and so on that perform particular tasks or implement particular abstract data types. The computing device 500 may be practiced in distributed cloud computing environments where tasks are performed by remote processing devices that are linked through a communications network. In a distributed cloud computing environment, program modules may be located in both, local and remote computer system storage media, including memory storage devices.

Referring now to FIG. 5, a block diagram of components of the computing device 500, in accordance with an embodiment of the present invention is shown. It should be appreciated that FIG. 5 provides only an illustration of an implementation and does not imply any limitations with regard to the environments in which different embodiments may be implemented. Many modifications to the depicted environment may be made.

The computing device may include one or more processors 502, one or more computer-readable RAMs 504, one or more computer-readable ROMs 506, one or more computer readable storage media 508, device drivers 512, read/write drive or interface 514, network adapter or interface 516, all interconnected over a communications fabric 518. Communications fabric 518 may be implemented with any architecture designed for passing data and/or control information between processors (such as microprocessors, communications and network processors, etc.), system memory, peripheral devices, and any other hardware components within a system.

One or more operating systems 510, and one or more application programs 511 are stored on one or more of the computer readable storage media 508 for execution by one or more of the processors 502 via one or more of the respective RAMs 504 (which typically include cache memory). In the illustrated embodiment, each of the computer readable storage media 508 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

The computing device may also include the R/W drive or interface 514 to read from and write to one or more portable computer readable storage media 526. Application programs 511 on the computing device may be stored on one or more of the portable computer readable storage media 526, read via the respective R/W drive or interface 514 and loaded into the respective computer readable storage media 508.

The computing device may also include the network adapter or interface 516, such as a TCP/IP adapter card or wireless communication adapter (such as a 4G wireless communication adapter using OFDMA technology). Application programs 511 may be downloaded to the computing device from an external computer or external storage device via a network (for example, the Internet, a local area network or other wide area network or wireless network) and network adapter or interface 516. From the network adapter or interface 516, the programs may be loaded onto computer readable storage media 508. The network may comprise copper wires, optical fibers, wireless transmission, routers, firewalls, switches, gateway computers and/or edge servers.

The computing device may also include a display screen 520, a keyboard or keypad 522, and a computer mouse or touchpad 524. Device drivers 512 interface to display screen 520 for imaging, to keyboard or keypad 522, to computer mouse or touchpad 524, and/or to display screen 520 for pressure sensing of alphanumeric character entry and user selections. The device drivers 512, R/W drive or interface 514 and network adapter or interface 516 may comprise hardware and software (stored on computer readable storage media 508 and/or ROM 506).

Additionally, chemical reaction control system 400 for executing multiple chemical experiments in parallel on an array of chemical reactors may be attached to the communications fabric 518.

Referring now to FIG. 7, illustrative cloud computing environment 700 is depicted. As shown, cloud computing environment 700 includes one or more cloud computing nodes 70 with which local computing devices used by cloud consumers, such as, for example, personal digital assistant (PDA) or cellular telephone 74A, desktop computer 74B, laptop computer 74C, and/or automobile computer system 74N may communicate. Cloud computing nodes 70 may communicate with one another. They may be grouped (not shown) physically or virtually, in one or more networks, such as Private, Community, Public, or Hybrid clouds as described hereinabove, or a combination thereof. This allows cloud computing environment 700 to offer infrastructure, platforms and/or software as services for which a cloud consumer does not need to maintain resources on a local computing device. It is understood that the types of computing devices 74A-N shown in FIG. 7 are intended to be illustrative only and that cloud computing nodes 710 and cloud computing environment 700 can communicate with any type of computerized device over any type of network and/or network addressable connection (e.g., using a web browser).

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

In a nutshell, the inventive concept may be summarized by the following clauses:

1. A method for executing multiple chemical experiments in parallel on an array of chemical reactors, the method comprising     receiving a list of actions to be performed for synthesizing a chemical product, wherein the list of actions corresponds to at least two chemical partial reactions, wherein the list comprises a delimiter symbol separating each two chemical partial reactions in the list of actions,     determining identical chemical partial reactions in the list of actions,     building a reaction commonality tree of the chemical partial reactions according to subsequent points in time in the list of actions, executing a plurality of the identical chemical partial reactions independent of a sequence of chemical partial reactions of the reaction commonality tree only once, wherein each of the plurality of identical chemical partial reactions is executed in a different reactor of the array of chemical reactors, wherein each resulting intermediate product has a quantity required by at least the sum of the related identical chemical partial reactions, and storing each complete quantity of identical related intermediate chemical products in a separate container, and executing non identical chemical partial reactions according to the reaction commonality tree, thereby using at least in parts the stored intermediate chemical products.

2. The method according to clause 1, also comprising
assigning a required number of the chemical reactors to one of the partial chemical reactions.

3. The method according to clause 1 or 2, wherein the assigning is performed under a constraint indicative of having more chemical partial reactions than chemical reactors available.

4. The method according to any of the preceding clauses, wherein the steps of receiving, determining, building and assigning is performed by a program service.

5. The method according to clause 4, wherein the program service is executable on a cloud computing system.

6. The method according to any of the preceding clauses, wherein the delimiter represents a store command.

7. The method according to any of the preceding clauses, wherein the chemical reactors are selected out of the group comprising batch reactors, continuous stirred tank reactors, plug flow reactors, semi-batch reactors, and microfluidic reactors.

8. The method according to any of the preceding clauses, also comprising
determining the quantity required by at least the sum of the related identical chemical partial reactions according to a function comprising at least one out of the following arguments: the sum of quantities required to synthesize the respective intermediate product, a first multiplication factor if the intermediate product is a solid compound, a second multiplication factor if the intermediate product is a liquid, or a third multiplication factor received from a user interface.

9. The method according to any of the preceding clauses, also comprising
producing one of the intermediate products in parallel in different ones of the chemical reactors.

10. The method according to any of the preceding clauses, wherein the chemical product is a plurality of chemical products.

11. A chemical reaction control system for executing multiple chemical experiments in parallel on an array of chemical reactors, the chemical reaction control system comprising
receiving means adapted for receiving a list of actions to be performed for synthesizing a chemical product, wherein the list of actions corresponds to at least two chemical partial reactions, wherein the list comprises a delimiter symbol separating each two chemical partial reactions in the list of actions,
determining means adapted for determining identical chemical partial reactions in the list of actions,
building means adapted for building a reaction commonality tree of the chemical partial reactions according to subsequent points in time in the list of actions,
first controlling means adapted for controlling an executing a plurality of the identical chemical partial reactions independent of a sequence of chemical partial reactions of the reaction commonality tree only once, wherein each of the plurality of identical chemical partial reactions is executed in a different rector of the array of chemical reactors, wherein each resulting intermediate product has a quantity required by at least the sum of the related identical chemical partial reactions, and
storage means adapted for storing each complete quantity of identical related intermediate chemical products in a separate container,
second controlling means adapted for controlling an executing of non-identical chemical partial reactions according to the reaction commonality tree, thereby using at least in parts the stored intermediate chemical products.

12. The chemical reaction control system according to clause 11, also comprising
assignment means adapted for assigning a required number of the chemical reactors to one of the partial chemical reactions.

13. The chemical reaction control system according to clause 11 or 12, wherein the assignment means are also adapted to be executed under a constraint indicative of having more chemical partial reactions than chemical reactors available.

14. The chemical reaction control system according to any of the clauses 11 to 13, wherein the receiving means, determination means, building means and assignment means are performed under control of a program service.

15. The chemical reaction control system according to clause 14, wherein the program service is executable on a cloud computing system.

16. The chemical reaction control system according to any of the clauses 11 to 15, wherein the delimiter represents a store command.

17. The chemical reaction control system according to any of the clauses 11 to 16, wherein the chemical reactors are selected out of the group comprising batch reactors, continuous stirred tank reactors, plug flow reactors, semi-batch reactors, and microfluidic reactors.

18. The chemical reaction control system according to any of the clauses 11 to 17, also comprising
determination means adapted for determining the quantity required by at least the sum of the related identical chemical partial reactions according to a function comprising at least one out of the following arguments: the sum of quantities required to synthesize the respective intermediate product, a first multiplication factor if the intermediate product is a solid compound, a second multiplication factor if the intermediate product is a liquid, or a third multiplication factor received from a user interface.

19. The chemical reaction control system according to any of the clauses 11 to 18, wherein the chemical reactors are also configurable for producing one of the intermediate products in parallel in different chemical reactors.

20. A computer program product for executing multiple chemical experiments in parallel on an array of chemical reactors, the program instructions being executable by one or more computing systems or controllers to cause the one or more computing systems to,
receive a list of actions to be performed for synthesizing a chemical product, wherein the list of actions corresponds to at least two chemical partial reactions, wherein the list comprises a delimiter symbol separating each two chemical partial reactions in the list of actions,
determine identical chemical partial reactions in the list of actions,
build a reaction commonality tree of the chemical partial reactions according to subsequent points in time in the list of actions,
control an execution of a plurality of the identical chemical partial reactions independent of a sequence of chemical partial reactions of the reaction commonality tree only once, wherein each of the plurality of identical chemical partial reactions is executed in a different reactor of the array of chemical reactors, wherein each resulting intermediate product has a quantity required by at least the sum of the related identical chemical partial reactions, and
storing each complete quantity of identical related intermediate chemical products in a separate container,
control an execution non identical chemical partial reactions according to the reaction commonality tree, whereby the stored chemical intermediates are at least partially used.

What is claimed is:

1. A method for executing multiple chemical experiments in parallel on an array of chemical reactors, the method comprising:
receiving a list of actions to be performed for synthesizing a chemical product, wherein the list of actions corresponds to at least two chemical partial reactions, wherein the list comprises a delimiter symbol separating each of the at least two chemical partial reactions in the list of actions;
determining identical chemical partial reactions in the list of actions;
building a reaction commonality tree of the chemical partial reactions according to subsequent points in time in the list of actions executing a plurality of the identical chemical partial reactions independent of a sequence of chemical partial reactions of the reaction commonality tree only once, wherein each of the plurality of identical chemical partial reactions is executed in a different reactor of the array of chemical reactors, wherein each resulting intermediate product has a quantity required by at least a sum of the related identical chemical partial reactions;
storing each complete quantity of identical related intermediate chemical products in a separate container; and
executing non identical chemical partial reactions according to the reaction commonality tree, thereby using at least in parts the stored intermediate chemical products.

2. The method according to claim 1, further comprising:
assigning a required number of the chemical reactors to one of the at least two chemical partial reactions.

3. The method according to claim 2, wherein
the assigning is performed under a constraint indicative of having more chemical partial reactions than chemical reactors available.

4. The method according to claim 2, wherein
the steps of receiving, determining, building and assigning is performed by a program service.

5. The method according to claim 4, wherein
the program service is executable on a cloud computing system.

6. The method according to claim 1, wherein
the delimiter represents a store command.

7. The method according to claim 1, wherein the chemical reactors are selected out of a group comprising batch reactors, continuous stirred tank reactors, plug flow reactors, semi-batch reactors, and microfluidic reactors.

8. The method according to claim 1, further comprising:
determining a quantity required by at least a sum of the related identical chemical partial reactions according to the function, the function comprising at least one out of the following: the sum of quantities required to synthesize the respective intermediate product, a first multiplication factor if the intermediate product is a solid compound, a second multiplication factor if the intermediate product is a liquid, and a third multiplication factor received from a user interface.

9. The method according to claim 1, further comprising:
producing one of the intermediate products in parallel in different ones of the chemical reactors.

10. The method according to claim 1, wherein
the chemical product is a plurality of chemical products.

11. A chemical reaction control system for executing multiple chemical experiments in parallel on an array of chemical reactors, the chemical reaction control system comprising:
a receiving means adapted for receiving a list of actions to be performed for synthesizing a chemical product, wherein the list of actions corresponds to at least two chemical partial reactions, wherein the list comprises a delimiter symbol separating each two chemical partial reactions in the list of actions;
a determining means adapted for determining identical chemical partial reactions in the list of actions;
a building means adapted for building a reaction commonality tree of the chemical partial reactions according to subsequent points in time in the list of actions;
a first controlling means adapted for controlling an executing a plurality of the identical chemical partial reactions independent of a sequence of chemical partial reactions of the reaction commonality tree only once, wherein each of the plurality of identical chemical partial reactions is executed in a different rector of the array of chemical reactors, wherein each resulting intermediate product has a quantity required by at least a sum of the related identical chemical partial reactions;
a storage means adapted for storing each complete quantity of identical related intermediate chemical products in a separate container; and
a second controlling means adapted for controlling an executing of non-identical chemical partial reactions according to the reaction commonality tree, thereby using at least in parts the stored intermediate chemical products.

12. The chemical reaction control system according to claim 11, further comprising:
an assignment means adapted for assigning a required number of the chemical reactors to one of the partial chemical reactions.

13. The chemical reaction control system according to claim 12, wherein
the assignment means are also adapted to be executed under a constraint indicative of having more chemical partial reactions than chemical reactors available.

14. The chemical reaction control system according to claim 12, wherein
the receiving means, the determination means, the building means and the assignment means are performed under control of a program service.

15. The chemical reaction control system according to claim 14, wherein
the program service is executable on a cloud computing system.

16. The chemical reaction control system according to claim 11, wherein
the delimiter represents a store command.

17. The chemical reaction control system according to claim 11, wherein
the chemical reactors are selected out of a group comprising batch reactors, continuous stirred tank reactors, plug flow reactors, semi-batch reactors, and microfluidic reactors.

18. The chemical reaction control system according to claim 11, further comprising:
a determination means adapted for determining the quantity required by at least a sum of the related identical chemical partial reactions according to the function comprising at least one out of the following arguments: the sum of quantities required to synthesize the respective intermediate product, a first multiplication factor if the intermediate product is a solid compound, a second multiplication factor if the intermediate product is a liquid, and a third multiplication factor received from a user interface.

19. The chemical reaction control system according to claim 11, wherein
the chemical reactors are also configurable for producing one of the intermediate products in parallel in different chemical reactors.

20. A computer program product for executing multiple chemical experiments in parallel on an array of chemical reactors, the computer program product comprising:
one or more computer-readable tangible storage media and program instructions stored on at least one of the one or more computer-readable tangible storage media, the program instructions executable by a processor, the program instructions being executable to:
receive a list of actions to be performed for synthesizing a chemical product, wherein the list of actions corresponds to at least two chemical partial reactions, wherein the list comprises a delimiter symbol separating each two chemical partial reactions in the list of actions;
determine identical chemical partial reactions in the list of actions;
build a reaction commonality tree of the chemical partial reactions according to subsequent points in time in the list of actions;
control an execution of a plurality of the identical chemical partial reactions independent of a sequence of chemical partial reactions of the reaction commonality tree only once, wherein each of the plurality of identical chemical partial reactions is executed in a different reactor of the array of chemical reactors, wherein each resulting intermediate product has a quantity required by at least a sum of related identical chemical partial reactions, and storing each complete quantity of identical related intermediate chemical products in a separate container; and
control an execution of non identical chemical partial reactions according to the reaction commonality tree, whereby the stored chemical intermediates are at least partially used.

* * * * *